(12) United States Patent
van Putten et al.

(10) Patent No.: US 12,138,395 B2
(45) Date of Patent: Nov. 12, 2024

(54) HEAT AND MOISTURE EXCHANGER

(71) Applicants: Blok Additive Manufacturing B.V., Nieuw Vennep (NL); Stichting Het Nederlands Kanker Instituut—Antoni van Leeuwenhoek Ziekenhuis, Amsterdam (NL)

(72) Inventors: Boris Theodore van Putten, Nieuw Vennep (NL); Bas Koper, Nieuw Vennep (NL); Sara Hillegonda Muller, Amsterdam (NL); Maartje Leemans, Amsterdam (NL); Maarten Jan Antony van Alphen, Amsterdam (NL)

(73) Assignees: Blok Additive Manufacturing B.V., Nieuw Vennep (NL); Stichting Het Nederlands Kanker Instituut—Antoni van Leeuwenhoek Ziekenhuis, Amsterdam (NL)

( * ) Notice: Subject to any disclaimer, the term of this patent is extended or adjusted under 35 U.S.C. 154(b) by 0 days.

(21) Appl. No.: 18/086,724

(22) Filed: Dec. 22, 2022

(65) Prior Publication Data

US 2023/0201513 A1     Jun. 29, 2023

(51) Int. Cl.
*A61M 16/10* (2006.01)
*B33Y 10/00* (2015.01)
(Continued)

(52) U.S. Cl.
CPC ...... *A61M 16/1045* (2013.01); *A61M 16/106* (2014.02); *B33Y 80/00* (2014.12);
(Continued)

(58) Field of Classification Search
CPC .... A61M 16/1045; A61M 16/106; F28F 7/02; F24F 3/147
See application file for complete search history.

(56) References Cited

U.S. PATENT DOCUMENTS 3,326,214 A * 6/1967 McCoy ............. A61M 16/1045
                                                165/4
3,965,695 A * 6/1976 Rush .................... F28D 19/042
                                                96/144

(Continued)

FOREIGN PATENT DOCUMENTS

EP        0255387 A2 *  2/1988
EP        387220 B2 *   4/2001 ........ A61M 16/1045
(Continued)

*Primary Examiner* — Kathryn E Ditmer
(74) *Attorney, Agent, or Firm* — N.V. Nederlandsch Octrooibureau

(57) ABSTRACT

A heat and moisture exchanger, comprises a rigid monolithic body (101). The rigid monolithic body (101) comprises a circumferential wall (102); and a structure of interconnected elements (106) surrounded by the circumferential wall (102). The structure (106) is open to fluid communication through the structure (106) between a first side (114) of the structure and a second side (115) of the structure (106) opposite the first side (114) of the structure (106). The circumferential wall (102) extends from the first side (114) to the second side (115) of the structure (106). The heat and moisture exchanger (100) is open on both of the first side (114) and the second side (115) of the structure (106), to allow fluid communication between the structure (106) and an exterior of the heat and moisture exchanger (100) on both sides (114, 115).

11 Claims, 3 Drawing Sheets

(51) Int. Cl.
    *B33Y 80/00*         (2015.01)
    *F28D 21/00*         (2006.01)
    *B22F 3/11*              (2006.01)
    *B22F 10/20*             (2021.01)

(52) U.S. Cl.
    CPC ..... *F28D 21/0015* (2013.01); *A61M 2207/00* (2013.01); *B22F 3/1115* (2013.01); *B22F 10/20* (2021.01); *B33Y 10/00* (2014.12)

(56) References Cited

U.S. PATENT DOCUMENTS

| | | | | | |
|---|---|---|---|---|---|
| 4,200,094 | A | * | 4/1980 | Gedeon | A61M 16/1045 128/201.13 |
| 4,271,110 | A | * | 6/1981 | Minjolle | F28F 21/04 264/209.1 |
| 4,325,365 | A | * | 4/1982 | Barbuto | A41D 13/0051 128/201.13 |
| 4,343,354 | A | * | 8/1982 | Weber | F28F 7/02 165/DIG. 395 |
| 4,746,479 | A | * | 5/1988 | Hanaki | F28F 7/02 264/150 |
| 5,010,594 | A | * | 4/1991 | Suzuki | A61M 16/1045 2/206 |
| 5,109,471 | A | * | 4/1992 | Lang | A61M 16/109 392/395 |
| 5,435,299 | A | * | 7/1995 | Langman | A62B 9/003 128/201.13 |
| 5,488,947 | A | * | 2/1996 | Frankel | A62B 9/003 128/207.14 |
| RE36,165 | E | * | 3/1999 | Behr | A61M 16/1045 128/201.13 |
| 5,937,856 | A | * | 8/1999 | Jonasson | A61M 16/1045 128/205.27 |
| 6,551,734 | B1 | * | 4/2003 | Simpkins | H01M 8/04074 429/495 |
| 2004/0261379 | A1 | * | 12/2004 | Bruun | F28F 9/0278 55/418 |
| 2006/0219397 | A1 | * | 10/2006 | Bruun | F28F 21/04 165/165 |
| 2014/0305431 | A1 | * | 10/2014 | Holley | A61M 16/06 128/205.24 |
| 2017/0198979 | A1 | * | 7/2017 | St. Rock | F28F 7/02 |
| 2018/0238627 | A1 | * | 8/2018 | Herring | F28F 13/08 |
| 2019/0024987 | A1 | * | 1/2019 | Moore | B33Y 80/00 |
| 2020/0003497 | A1 | * | 1/2020 | Aston | F28F 7/02 |
| 2020/0300561 | A1 | * | 9/2020 | Walter | F28F 9/026 |
| 2020/0405994 | A1 | | 12/2020 | Shirley et al. | |
| 2022/0260316 | A1 | * | 8/2022 | Becker | F28F 7/02 |
| 2023/0158269 | A1 | * | 5/2023 | Harrison, IV | A61M 16/1055 128/203.26 |

FOREIGN PATENT DOCUMENTS

| | | | | |
|---|---|---|---|---|
| EP | 3479876 A1 | * | 5/2019 | ........ A61M 16/0066 |
| GB | 2540456 A | * | 1/2017 | ........ A61M 16/1045 |
| JP | S60246767 A | * | 12/1985 | |
| JP | H0221161 A | * | 1/1990 | |
| SE | 467289 B | * | 6/1992 | ........... A61M 16/04 |
| WO | WO-9103277 A | * | 3/1991 | ........ A61M 16/1045 |
| WO | 2015/013761 A1 | | 2/2015 | |
| WO | WO-2022203523 A1 | * | 9/2022 | |

\* cited by examiner

HEAT AND MOISTURE EXCHANGER

FIELD OF THE INVENTION

The invention relates to a heat and moisture exchanger. The invention further relates to a method of manufacturing a heat and moisture exchanger.

BACKGROUND OF THE INVENTION

A passive heat and moisture exchanger (HME) is a device that can be used to aid breathing, for example for patients after tracheotomy or after laryngectomy. Such a HME helps to humidify the inhaled air and sometimes it has a filter function. Some HMEs can also facilitate closure of the stoma to allow speaking. Compared to HMEs that are used in ventilation systems, the space that is available for a HME that is directly connected to a stoma is restricted. As a result, there is a trade-off between the HME's dimensions, humidification capacity and breathing resistance.

"Ex Vivo Assessment and Validation of Water Exchange Performance of 23 Heat and Moisture Exchangers for Laryngectomized Patients", by C. van den Boer., MD., et al., in: Respiratory care, August 2014, Vol. 59, No. 8, pp. 1161-1171, discloses that HMEs consist of a functional core material (usually a foam, sometimes coated with hygroscopic salt) contained in a cassette. The functional core material traps and releases a small amount of water during exhalation and inhalation, respectively.

It would be advantageous to provide an improved heat and moisture exchanger.

SUMMARY OF THE INVENTION

To better address this concern, a first aspect of the invention provides a heat and moisture exchanger, comprising a rigid monolithic body, wherein the rigid monolithic body comprises:
  a circumferential wall; and
  a structure of interconnected elements surrounded by the circumferential wall, wherein the structure is open to fluid communication through the structure from a first side of the structure to a second side of the structure opposite the first side of the structure,
  wherein the circumferential wall extends around the structure from the first side to the second side of the structure,
  wherein the heat and moisture exchanger is open on both of the first side and the second side of the structure, to allow fluid communication between the structure and an exterior of the heat and moisture exchanger on both sides.

The structure of interconnected elements acts as a buffer for storing moisture from exhaled air, which is absorbed by the inhaled air, so that the inhaled air is humidified. By implementing the circumferential wall and the structure as a monolithic object, it is no longer necessary to insert a separate core material in a HME. The production may be more efficient, and the durability of the HME may be improved by this.

For example, the rigid monolithic body comprises a metal. A metal is particularly durable. Moreover, the structure of interconnected elements, comprising metal, has excellent heat capacity to store and exchange sufficient moisture by condensation on the surface of the interconnected elements of the structure and subsequent evaporation into the inhaled air.

The rigid monolithic body may be made by metal additive manufacturing. This provides a particularly efficient production technology. It allows a refined design of in particular the structure of interconnected elements.

Inside the structure of interconnected elements, a distance from any point to a nearest element of the structure may be, for example, at most 1.5 millimeters, preferably at most 1 millimeter. This way, it may be guaranteed that the surface area of the structure of interconnected elements is sufficiently large for exchange of heat and moisture.

The structure of interconnected elements may form a plurality of parallel channels connecting the first side of the structure to the second side of the structure. The channels have a large surface area for exchange of heat and moisture. At the same time, they have relatively small flow resistance, thereby making breathing easy and/or comfortable.

A diameter of the plurality of parallel channels may be in a range from 0.5 millimeter to 2 millimeters. This may be a suitable dimension to achieve desirable heat and moisture exchange and flow resistance.

The rigid monolithic body further comprises a fluid guide at the first open side of the structure of interconnected elements, said fluid guide comprising a wall covering at least part of the first open side and at least one opening oriented obliquely away from the first open side. By virtue of the openings, the fluid guide guides the air flow in a direction that may be favorable for convenience, by for example avoiding clothing to be attracted into the heat and moisture exchanger or avoid direct exposure to wind.

The at least one opening may be, in a particularly advantageous example, two openings. These two openings may be oriented obliquely away from the first open side and oriented obliquely away from each other at opposite angles. The oblique angle helps to avoid clothing to be attracted into the heat and moisture exchanger or avoid direct exposure to wind. Moreover, the two openings oriented obliquely away from each other at opposite angles makes it convenient to close both openings simultaneously with two fingers of a hand.

Each of the at least one opening may be at most 1.5 cm in maximum diameter, so that each opening can be closed by a typical human finger.

The structure may be connected to the fluid guide in between the two openings. This feature may provide a support for the fluid guide to enhance the strength of the heat and moisture exchanger. Moreover, this feature may improve the production process using additive manufacturing.

The structure may comprise a passage near the fluid guide, wherein the passage allows fluid communication between the two openings. For example, the passage may be provided in the support. The fluid passage may prevent occurrence of a pressure difference on both sides of the support.

The heat and moisture exchanger may further comprise a polymer cover with a shape corresponding to a shape of the fluid guide, the cover comprising at least one opening matching each of the at least one opening of the fluid guide, wherein the cover and the rigid monolithic body have engaging elements to fixate the cover on top of the fluid guide. Thus, the polymer cover is not part of the monolithic body. Moreover, since the polymer cover may be replaced at will it can keep the visible front free from traces of tear and wear, can be adapted to current fashion or currently worn clothes. Moreover, special covers can be designed to provide protection for special activities such as showering or sleeping.

The circumferential wall of the rigid monolithic body may comprise a coupling member for engaging with a corresponding coupling member provided in an adhesive or a cannula, to fixate the heat and moisture exchanger to the adhesive pad or the cannula. This facilitates easy fixation of the heat and moisture exchanger at the proper place in respect of the patient. In certain embodiments, the adhesive may be an adhesive pad.

The heat and moisture exchanger may comprise such an adhesive with the corresponding coupling member, wherein the adhesive comprises a through hole corresponding to the second open side of the structure and an adhesive area around the through hole for attaching the adhesive to a patient. Such an adhesive allows to attach the heat and moisture exchanger to the patient by adhesion.

According to another aspect of the invention, a method is provided to produce a heat and moisture exchanger. The method comprises producing a rigid monolithic body of a heat and moisture exchanger by additive manufacturing, wherein the rigid monolithic body comprises:

a circumferential wall; and a structure of interconnected elements surrounded by the circumferential wall, wherein the structure is open to fluid communication through the structure from a first side of the structure to a second side of the structure opposite the first side of the structure, wherein the circumferential wall extends around the structure from the first side to the second side of the structure, wherein the heat and moisture exchanger is open on both of the first side and the second side of the structure, to allow fluid communication between the structure and an exterior of the heat and moisture exchanger on both sides.

The person skilled in the art will understand that the features described above may be combined in any way deemed useful. Moreover, modifications and variations described in respect of the heat and moisture exchanger may likewise be applied to the method of manufacturing the heat and moisture exchanger, and modifications and variations described in respect of the method may likewise be applied to the heat and moisture exchanger.

BRIEF DESCRIPTION OF THE DRAWINGS

In the following, aspects of the invention will be elucidated by means of examples, with reference to the drawings. The drawings are diagrammatic and may not be drawn to scale. Throughout the drawings, similar items may be marked with the same reference numerals.

DETAILED DESCRIPTION OF EMBODIMENTS

Figure 1:
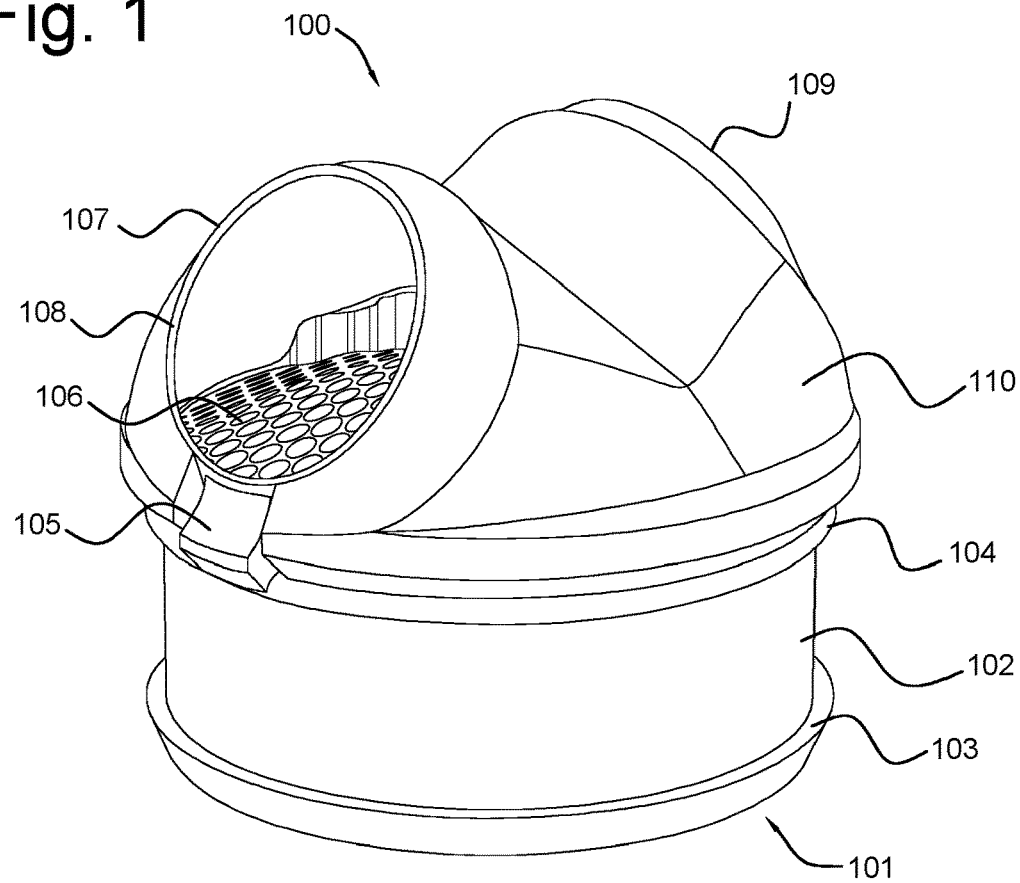
FIG. 1 shows a perspective view of a heat and moisture exchanger.

Certain exemplary embodiments will be described in greater detail, with reference to the accompanying drawings. The matters disclosed in the description, such as detailed construction and elements, are provided to assist in a comprehensive understanding of the exemplary embodiments. Accordingly, it is apparent that the exemplary embodiments can be carried out without those specifically defined matters. Also, well-known operations or structures are not described in detail, since they would obscure the description with unnecessary detail.

The heat and moisture exchanger may comprise a rigid monolithic body. This rigid monolithic body may comprise both a structure of interconnected elements and a circumferential wall around the structure of interconnected elements. The structure of interconnected elements may be regarded a humidification section, as it is realizes the humidification of the inhaled air.

In certain embodiments, the circumferential wall may encircle the structure of interconnected elements and extend from the first site to the second side of the structure, without any openings. The circumferential wall may extend from the first side of the structure to the second side of the structure, leaving the first side of the structure and the second side of the structure open. In certain embodiments, the circumferential wall ensures that inhaled air and exhaled air passes through the whole of the structure of interconnected elements and cannot escape on the side in between the first side and the second side.

Also, at least part of the circumferential wall may be thicker than a thickness of the interconnected elements, so that the circumferential wall provides strength to the HME and protects the potentially weaker structure of interconnected elements. Moreover, the material of the wall can improve the performance of the heat and moisture exchanger by providing additional heat capacity.

The structure of interconnected elements is open in the sense that it provides passage for air entering the structure at the first side of the structure to leave the structure at the second side of the structure, and vice versa, it provides passage for air entering the structure at the second side of the structure to leave the structure at the first side of the structure. At the same time, the circumferential wall may fluidly close the rigid monolithic body in between the first side and the second side.

In the present disclosure, where "fluid" is mentioned, "air" may be considered to be a suitable example of the "fluid", as it may correspond to the common use of the HME. Thus, in certain embodiments, fluid flow may be understood as airflow, "fluidly connected" may be understood as allowing in particular airflow, "fluidly closed" may be understood as airtight closed, and fluid guide may be understood as air guide.

In the subsequently described detailed embodiments, the monolithic body is made of a metal. However, this is not a limitation. The monolithic body may alternatively be made of any other suitable, biocompatible material or composition. Such a material could be a polymer or a ceramic, for example. Preferably the monolithic body is made by additive manufacturing (3D printing), but an alternative manufacturing method may be casting, molding, or milling.

In certain embodiments, the rigid monolithic body is made of a metal or alloy. Preferably the used metal is, as much as possible, corrosion free and/or biocompatible. Examples of suitable metals are stainless steel, titanium, aluminum, and precious metals such as gold, silver, or platina. Also a suitable alloy can be used as the material. For example, an aluminum alloy or a titanium alloy.

In certain embodiments, the rigid monolithic body is manufactured by means of additive manufacturing. For example, the rigid monolithic body is designed using a computer aided design program, and the design is input to a 3D printer that can print the rigid monolithic body as a 3D metal object. Thus, the configuration of the interconnected elements, including their shape and their connections, may be designed beforehand as part of the computer aided design process.

The heat capacity is an important property of the heat and moisture exchanger. The volume and mass of the material used and the surface area in contact with the inhaled and exhaled air are important parameters that can be controlled in the design to obtain desired exchange properties. To facilitate exchange of heat and moisture, a large contact surface area is important. Therefore, the distance between the interconnected elements is preferably kept sufficiently small. At the same time, the resistance to air may be kept low, or at least within an acceptable range. For example, the distance from any point (in the air-filled spaces between the interconnected elements) to the nearest part of the structure of interconnected elements is at most 1.5 millimeters, preferably 1 millimeter, more preferably 0.5 millimeter, even more preferably 0.25 millimeter. On the other hand, to avoid too much flow resistance, the same distance is preferably not less than 0.1 millimeter, preferably not less than 0.2 millimeter. All in all in certain embodiments the range for said distance may be in the range of 0.1 millimeter to 1.5 millimeters, preferably in the range of 0.1 millimeter to 1 millimeter, more preferably in the range of 0.2 millimeter to 0.5 millimeter, even more preferably in the range of 0.2 to 0.25 millimeter.

In certain embodiments the structure of interconnected elements may be, for example, a plurality of rods or bullets or other geometric shapes that are interconnected at certain touch points. The arrangement of the interconnected elements may be erratic, or may be regularly arranged, in a grid for example.

In certain other embodiments, the structure of interconnected elements may provide unobstructed line-of-sight in channels extending from the first side to the second side. This helps to keep the air flow resistance low. For example, the structure of interconnected elements may form a plurality of parallel channels, each channel providing unobstructed flow through the channel from the first side of the structure to the second side of the structure. In certain embodiments, the diameter of these channels may be in a range from 0.5 millimeter to 2 millimeters.

In certain embodiments, the monolithic object comprises the structure of interconnected elements, the circumferential wall, and a fluid guide at the first open side of the structure of interconnected elements. The fluid guide may cover the first side of the structure and guide exhaled air towards at least one opening. The fluid guide may be attached to the circumferential wall all around the circumferential wall at the first side of the structure. This way, any air can flow in and out of the structure at the first side only via dedicated openings in the fluid guide.

This fluid guide may be curved. Also, there may be a distance in between (most of the) interconnected elements and the fluid guide. Such a distance may particularly be provided where the structure of interconnected elements consist of a plurality of parallel channels.

The fluid guide has at least one opening. In certain embodiments this opening is oriented at an angle away from the first open side. For example the at least one opening may be oriented obliquely, for example diagonally, with respect to the first open side. For example, an angle between a normal of the first side and a normal of the opening may be in a range of 25 degrees to 90 degrees, preferably in a range of 40 to 60 degrees. In the present disclosure the normal of an opening will be understood as the normal of a plane fitted to the edge of the opening.

Each opening of the fluid guide is preferably sized so that it can be closed by being covered by a single human finger. For example, each opening is at most 16 mm in diameter. If the opening is noncircular, a smallest diameter is preferably at most 16 mm and a largest diameter is preferably at most 20 mm.

In certain embodiments, the fluid guide has at least two openings, oriented away from each other. For example, an angle between a first normal of the first opening and a second normal of the second opening is at least 75 degrees, preferably 90 degrees.

In between the at least two openings, the fluid guide may at least partially have a saddle shape. In between the at least two openings, the fluid guide may be connected to the structure of interconnected elements, which can provide a support to improve the strength of the HME. Further, especially if the structure of interconnected elements does not allow lateral flow through the structure, one or more openings may be provided in the structure of interconnected elements close to the fluid guide, to allow lateral flow from one opening to the other, to equalize any pressure difference on both sides of the support.

The rigid monolithic body can have several coupling members to couple the rigid monolithic body to further components. For example, coupling members may be provided to place a cover over the first side (optionally over the fluid guide). Also, coupling members may be provided to fix the rigid monolithic body to a carrier that attaches to the patient.

A cover (or cap) may be made of a polymer and may correspond in shape to the shape of the fluid guide. The cover may also have connection members engaging with corresponding connection members on the rigid monolithic body so it can be attached on top of the first side of the structure of interconnected elements and/or on top of the fluid guide. The cover may also have a shape that provides an additional fluid guide optimized for a special activity, on top of the (optional) fluid guide of the rigid monolithic body.

Different carriers may be used to properly attach the HME to the patient. The HME may fit in such a carrier and may have tabs and/or edges extending therefrom to fixate it in a slot of the plaster and to prevent that the HME is pushed too far through the carrier. For example, the tabs and/or edges may extend from the outside of the circumferential wall.

For example, an adhesive may be used that has a hole matching the second side of the structure of interconnected elements. This adhesive may comprise, for example, acryl, hydrogel and/or hydrocolloid. The adhesive may have a rigid ring around the hole of the adhesive. This rigid ring may have coupling members that engage with corresponding coupling members of the rigid monolithic body. For example a clamping ridge and a placement ridge may extend from an outside of the circumferential wall that engages with corresponding recesses in the rigid ring of the adhesive pad. However, this is just an example. The adhesive may be an adhesive pad. It will be understood that different types of carrier and different types of adhesive may be employed.

Alternatively, the carrier may be a cannula. The cannula may have coupling members engaging with corresponding coupling members on the rigid monolithic body, preferably on the outside of the circumferential wall. Preferably, the rigid monolithic body comprises coupling members that are compatible with both the adhesive and the cannula, for flexible use.

The HME disclosed in the present disclosure, in particular the rigid monolithic body of the HME, may be cleanable. For example, an ultrasonic bath or ultrasonic cleaning device may be used to clean the structure of interconnected elements. In certain embodiments, a cleaning agent is applied during the ultrasonic cleaning process. For example, the HME may be cleaned in the ultrasonic bath in a bath with a cleaning agent. Therefore, such an ultrasonic cleaning device may be provided with the HME for use with the HME by a patient. A kit of parts therefore may include an ultrasonic cleaning device and a HME as disclosed herein. An ultrasonic cleaner is known by itself for the purpose of, for example, eyeglass cleaning).

In certain embodiments, the HME, in particular the rigid monolithic body of the HME, may optionally be disinfected, for example in a bath of a suitable detergent, such as isopropylalcohol.

By using additive manufacturing of a metal, the HME can be produced in a cost effective manner. Because a metal HME, with dimensions comparable to other small passive HMEs, has a larger heat capacity, a significantly improved performance can be realized in terms of higher performance at an acceptable breathing resistance.

The metal HME does not rely on a hygroscopic salt coating, as other passive hygroscopic HMEs do. The end user can therefore clean the HME him/herself, at home, using an ultrasound cleaner, without negatively affecting the performance of the HME. The metal HME is durable and reusable. Because of this, in practice the HME can be more cost efficient than a daily disposable HME.

The one or two openings that are directed away from each other at an angle (for example diagonally), provide a relatively large opening for the flow of air, thereby keeping the flow resistance low. Because of this, the end user does not have to replace or remove the HME at times of physical exertion, while allowing the HME to keep providing the appropriate conditioning of the inhaled air.

The one or two openings are small enough so that they can be closed by the fingers. For example, each opening has a size so that it can be covered by a human finger, in particular a human adult finger. For example a diameter of about 1 cm may be employed. For children other size can be adopted. For example the opening may be circular or oval.

The position of the opening as a hole in the HME, directed at an angle away from the filter structure, helps to reduce the likelihood that clothing is sucked into the HME during inhaling, which would potentially block the airflow. Also, wind would not blow directly into the HME by virtue of the angle. The angle may be, for example, 45 degrees. Alternatively, it may be between 30 to 90 degrees, preferably between 30 to 60 degrees.

In daily practice, the metal HME is easy to attach to the adhesive by virtue of attachment means. Since the HME is light weight, the HME and the adhesive remains in place during use.

A method of producing a heat and moisture exchanger comprises producing a rigid monolithic body of a heat and moisture exchanger by additive manufacturing, wherein the rigid monolithic body comprises a circumferential wall and a structure of interconnected elements surrounded by the circumferential wall, as described herein. The method may comprise designing a 3D model of the monolithic rigid body, importing the 3D model in a 3D printer, and 3D printing the rigid monolithic body, preferably by metal additive manufacturing.

In the following, details of an embodiment of the present invention will be elaborated with reference to the drawings. However it will be understood that these details do not limit the present invention and the embodiment is presented to illustrate, rather than limit the features of the present invention.

FIG. 1 shows a perspective view of a heat and moisture exchanger 100. Visible components include a rigid monolithic body 101 that comprises a circumferential wall 102 around a structure of interconnected elements 106. The structure of interconnected elements 106 provides the HME 100 with a humidification function, in particular with a moisture exchanging function. From the outside of the circumferential wall 102, a first circumferential ridge 103 and a second circumferential ridge 104 extends. These ridges are to clamp the HME 100 to a carrier. Further, tabs 105 extend from the rigid monolithic body 101 to prevent the HME 100 from being pushed through the carrier too far.

Figure 2:
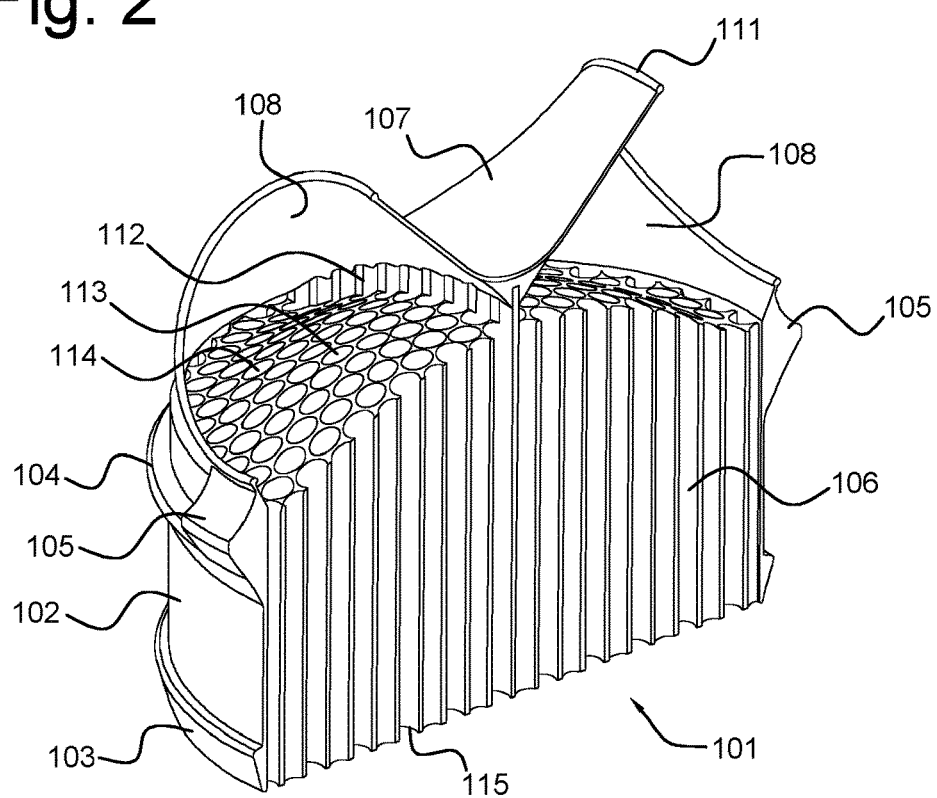
FIG. 2 shows an oblique section view of a rigid monolithic body of the heat and moisture exchanger.

FIG. 2 shows an oblique section view showing the rigid monolithic body 101 in greater detail. The structure of interconnected elements 106 is realized in form of a plurality of parallel cylindrical channels. The walls around each channel can be considered to be the interconnected elements, and the channels are connected to their neighboring channels. The ends 113 of the channels at the first side 114 and/or at the second side 115 of the structure of interconnected elements 106 may be chamfered. This may reduce drag.

The rigid monolithic body 101 comprises a fluid guide 107 that covers the first side 114 of the structure of interconnected elements 106 and is fixed to the edge of the circumferential wall 102. The fluid guide 107 comprises two openings (through holes) 108. In between the two openings 108, the fluid guide has a saddle shape, being closest to the structure of interconnected elements 106 in between the two openings 108 and extending away from the structure of interconnected elements the furthest at the edge 111 of the openings 108. In the shown example, the fluid guide 108 is connected to the structure of interconnected elements 106. To that end, the structure of interconnected elements 106 has a supporting bridge 112 extending from the first side 114 of the structure of interconnected elements 106. The supporting bridge 112 is connected to the fluid guide 107. The edge 111 of the openings 108 may be rounded for convenient touch when closing the openings 108 using the fingers.

Figure 3:
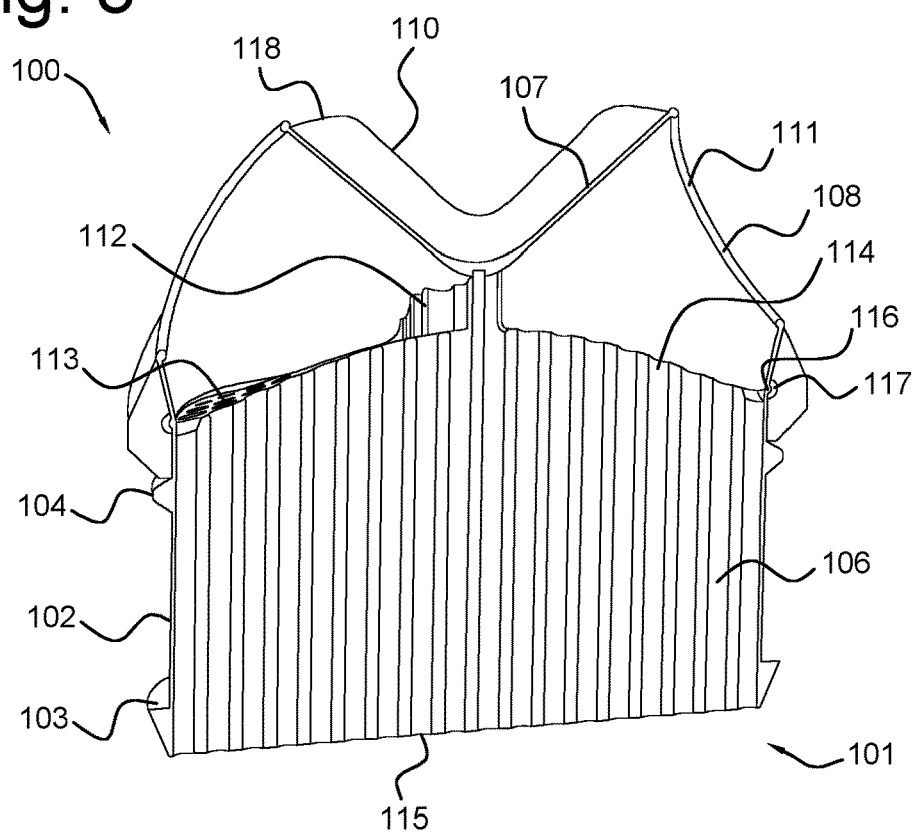
FIG. 3 shows a first section view of the heat and moisture exchanger showing two openings.

FIG. 3 shows a first section view of the heat and moisture exchanger showing the two openings 108 and the removable cover 110. The cover 110 covers the fluid guide 107. The edges 111 of the openings 108 of the fluid guide 107 extend beyond the edges 118 of the corresponding openings of the cover. This allows proper closure of the holes 108 in the fluid guide 107 by the fingers. The rigid monolithic body 101 has coupling member 116 and the cover 110 has coupling member 117. Coupling members 116 and 117 engage to fix the cover 110 on top of the fluid guide 107. The coupling members may comprise a protruding edge and a corresponding recess, for example.

Figure 4:
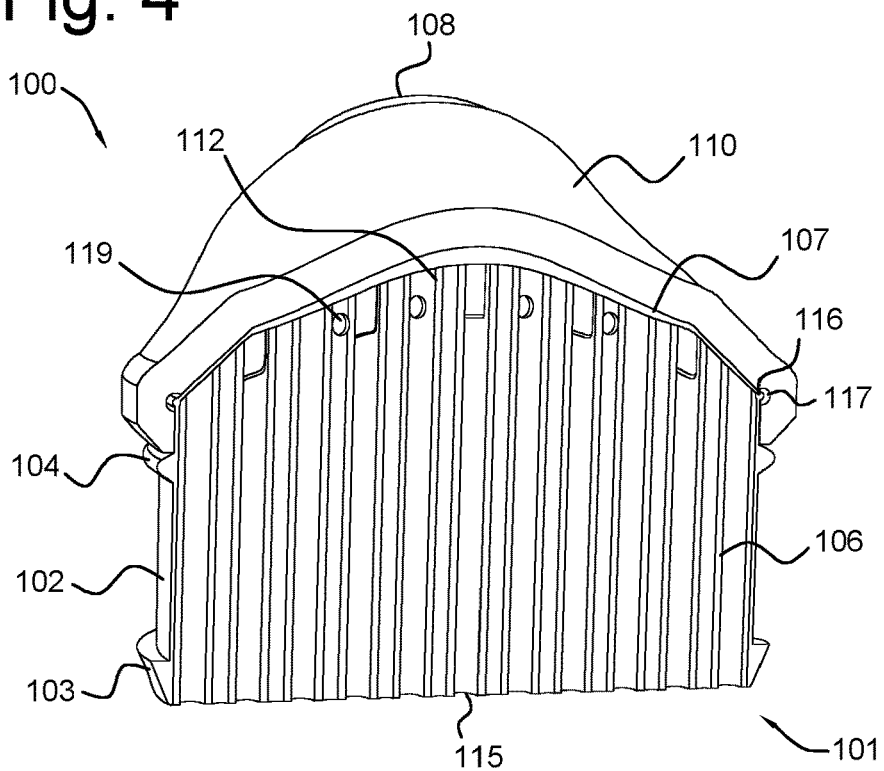
FIG. 4 shows a second section view of the heat and moisture exchanger showing a support.

FIG. 4 shows a second section view of the heat and moisture exchanger. In FIG. 4, the support bridge 112, as a particular example of a support, can be best observed. The support bridge 112 extends beyond the first side 114 of the structure of interconnected elements 106 and is connected to the fluid guide 107 in between the openings 108. As illustrated, the support bridge 112 comprises one or more fluid passages 119 in form of openings in the support bridge 112. This can avoid any pressure difference on both sides of the support bridge 112.

Figure 5:
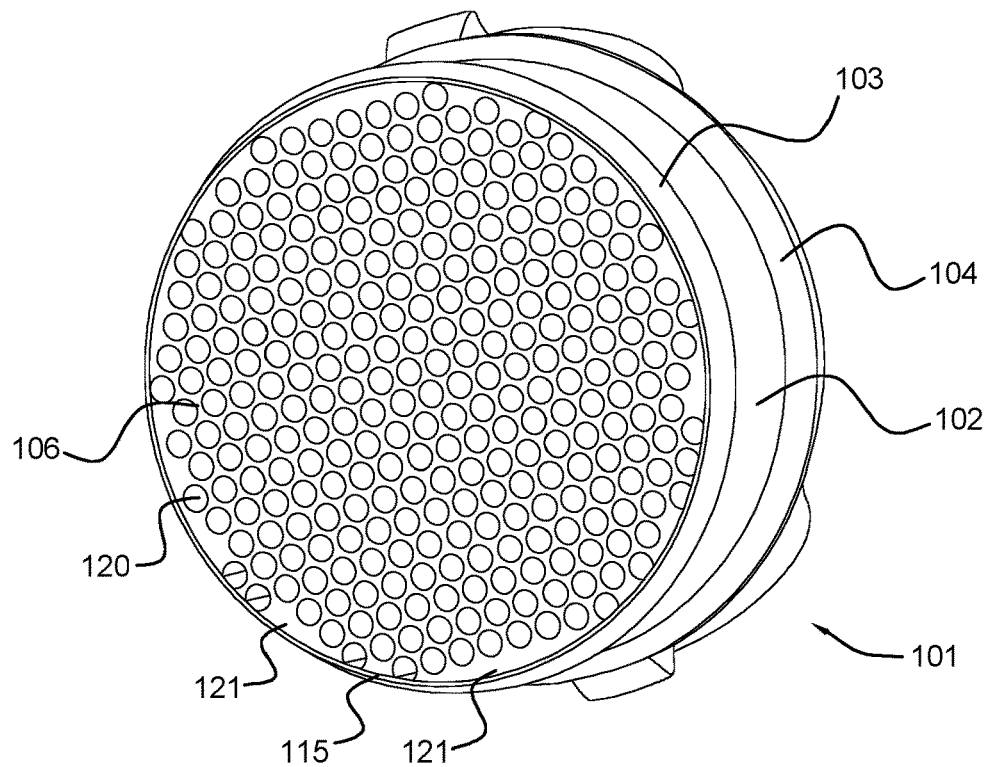
FIG. 5 shows another perspective view showing of the rigid monolithic body.

FIG. 5 shows another perspective view showing of the rigid monolithic body. FIG. 5 shows the second side 115 of the monolithic body in greater detail. In particular an example arrangement of cylindrical channels 120 through the metal of the structure of interconnected elements 106 is shown. Also some portions 121 of the circumferential wall 102 may be thicker than the interconnected elements 106 in between neighbouring channels 120, thus providing additional heat capacity. As illustrated in the shown example, the outside surface of the circumferential wall 102 may be cylindrical.

Figure 6:
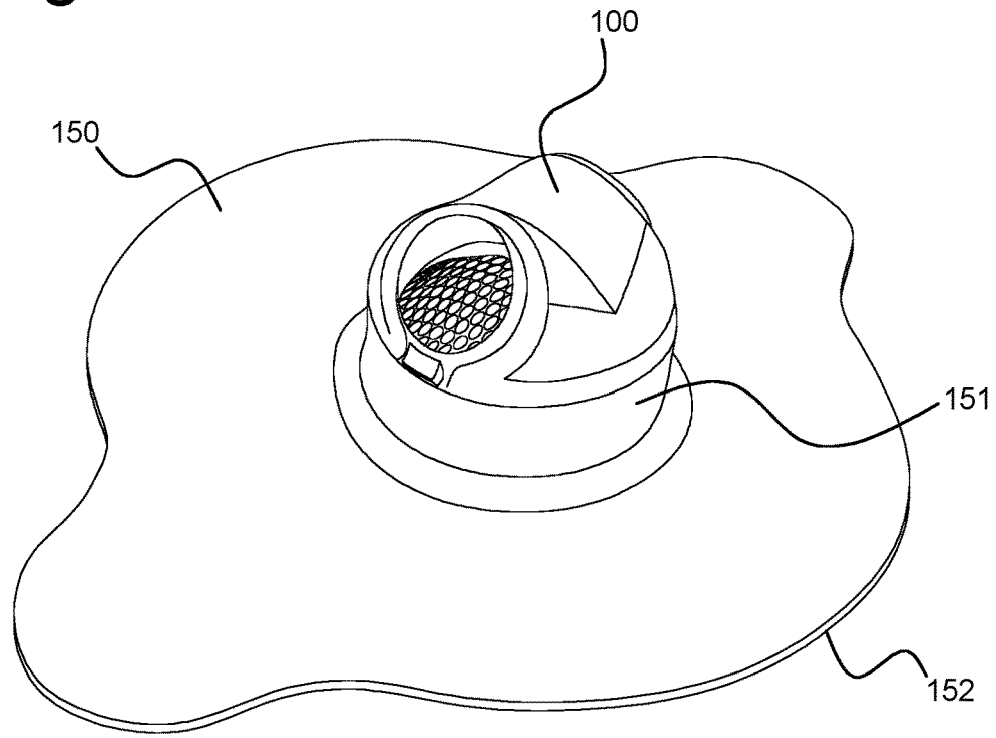
FIG. 6 shows the heat and moisture exchanger mounted on an adhesive.

FIG. 6 shows the heat and moisture exchanger 100 mounted on an adhesive 150. Adhesive 150 may be made of a textile or another carrier material and may have an adhesive layer (152) on a side facing away from the heat and moisture exchanger 100. Also, the adhesive 150 has a through hole with along the edge of the through hole a reinforced cylindrical holder 151, which may be made of a polymer or a metal. The inner diameter of the cylindrical holder 151 corresponds to the outer diameter of the circumferential 102 wall of the cylindrical heat and moisture exchanger 100, so that the heat and moisture exchanger 100 fits tightly in the cylindrical holder 151 so that no significant amount of fluid can flow through the opening of the adhesive 150 except through the heat and moisture exchanger. In case of non-cylindrical design, the hole and reinforced holder's dimensions match the dimensions of the heat and moisture exchanger to achieve the same effect.

As described before, the heat and moisture exchanger 100 may alternatively be employed in conjunction with a different carrier, for example an interface to connect to a cannula.

Tests were performed to validate the cleaning and performance of the heat and moisture exchanger disclosed herein. The repeated cleaning procedure of the HME (a combination of ultrasonic cleaning and a commercially available dental tablet) satisfies the acceptance criteria for reusable medical devices according to AAMI TIR 30, disclosed by the Association for the Advancement of Medical Instrumentation. AAMI TIR 30: "A compendium of processes, materials, test methods, and acceptance criteria for cleaning reusable medical devices", 46. After cleaning, the tested devices appeared visibly clean and contained no to little residual protein or carbohydrates. Moreover, the HME was not considered to have a cytotoxic potential after cleaning and disinfection (all lifetime cycles) according to the ISO 10993-5 guidelines.

The moisture loss of the HME disclosed herein is better in comparison to a commercially available HME, consisting of a foam layer with salt, with equal diameter (22 mm) and comparable breathing resistance (pressure drop) as presented in the table below. Testing was performed in an external lab according to the ISO 9360-2 guidelines.

| HME | Moisture loss [mg/L] $44/0\ _{mg/L}$, $V_T = 1\ L$ | Pressure drop [hPa] 30 L/min | 60 L/min | 90 L/min |
|---|---|---|---|---|
| PURINOX HME | 15.3 | 0.5 | 1.3 | 2.7 |
| Commercially available HME with 22 mm diameter | 24.0 | 0.4 | 1.3 | 2.9 |

The examples and embodiments described herein serve to illustrate rather than limit the invention. The person skilled in the art will be able to design alternative embodiments without departing from the spirit and scope of the present disclosure, as defined by the appended claims and their equivalents. Reference signs placed in parentheses in the claims shall not be interpreted to limit the scope of the claims. Items described as separate entities in the claims or the description may be implemented as a single hardware or software item combining the features of the items described.

The invention claimed is:

1. A heat and moisture exchanger, comprising a rigid monolithic body, wherein the rigid monolithic body comprises:
   a circumferential wall; and
   a structure of interconnected elements surrounded by the circumferential wall, wherein the structure is open to fluid communication through the structure between a first side of the structure and a second side of the structure opposite the first side of the structure,
   wherein the circumferential wall extends from the first side to the second side of the structure,
   wherein the heat and moisture exchanger is open on both of the first side and the second side of the structure, to allow fluid communication between the structure and an exterior of the heat and moisture exchanger on both of the first and second sides,
   wherein the rigid monolithic body further comprises a fluid guide at the first side of the structure of interconnected elements, the fluid guide comprising a wall covering at least part of the first side and at least one opening oriented obliquely away from the first side,
   wherein the at least one opening is two openings, oriented obliquely away from the first side and oriented away from each other at opposite angles,
   wherein the structure is connected to the fluid guide in between the two openings, and
   wherein the structure comprises a passage near the fluid guide, wherein the passage allows fluid communication between the two openings.

2. The heat and moisture exchanger according to claim 1, wherein the rigid monolithic body comprises a metal.

3. The heat and moisture exchanger according to claim 1, wherein the rigid monolithic body is made by additive manufacturing.

4. The heat and moisture exchanger according to claim 1, wherein inside the structure a distance from any point to a nearest element of the structure is at most 1.5 millimeters.

5. The heat and moisture exchanger according to claim 1, wherein the structure of interconnected elements forms a plurality of parallel channels connecting the first side of the structure to the second side of the structure.

6. The heat and moisture exchanger according to claim 1, wherein a diameter of each channel of the plurality of parallel channels is in a range from 0.5 millimeter to 2 millimeters.

7. The heat and moisture exchanger according to claim 1, wherein each of the at least one opening has a shortest diameter of at most 16 millimeters.

8. A method of producing a heat and moisture exchanger according to claim 1, comprising
   producing a rigid monolithic body of the heat and moisture exchanger by additive manufacturing, wherein the rigid monolithic body is made of a single biocompatible material or composition, wherein the rigid monolithic body comprises:
   a circumferential wall; and
   a structure of interconnected elements surrounded by the circumferential wall, wherein the structure is open to fluid communication through the structure from a first side of the structure to a second side of the structure opposite the first side of the structure, wherein the structure of interconnected elements forms a plurality of parallel channels connecting the first side of the structure to the second side of the structure, wherein the circumferential wall extends around the structure from the first side to the second side of the structure, wherein the heat and moisture exchanger is open on both of the first side and the second side of the structure, to allow fluid communication between the structure and an exterior of the heat and moisture exchanger on both of the first and second sides, wherein the rigid monolithic body further comprises a fluid guide at the first side of the structure of interconnected elements, the fluid guide comprising a wall covering at least part of the first side and at least one opening oriented obliquely away from the first side, wherein the at least one opening is two openings, oriented obliquely away from the first side and oriented away from each other at opposite angles, and wherein the structure comprises a passage near the fluid guide, wherein the passage allows fluid communication between the two openings.

9. A heat and moisture exchanger, comprising a rigid monolithic body, wherein the rigid monolithic body comprises:

a circumferential wall; and a structure of interconnected elements surrounded by the circumferential wall, wherein the structure is open to fluid communication through the structure between a first side of the structure and a second side of the structure opposite the first side of the structure, and a fluid guide at the first side of the structure of interconnected elements, said fluid guide comprising a wall covering at least part of the first side and at least one opening oriented obliquely away from the first side, wherein the circumferential wall extends from the first side to the second side of the structure, wherein the heat and moisture exchanger is open on both of the first side and the second side of the structure, to allow fluid communication between the structure and an exterior of the heat and moisture exchanger on both of the first and second sides, and wherein the heat and moisture exchanger further comprises a polymer cover with a shape corresponding to a shape of the fluid guide, the cover comprising at least one opening matching each of the at least one opening of the fluid guide, wherein the cover and the rigid monolithic body have engaging elements to fixate the cover on top of the fluid guide.

10. The heat and moisture exchanger according to claim 9, wherein the circumferential wall comprises a coupling member for engaging with a corresponding coupling member provided in an adhesive or a cannula, to fixate the heat and moisture exchanger to the adhesive or the cannula.

11. The heat and moisture exchanger according to claim 10, further comprising the adhesive with the corresponding coupling member, wherein the adhesive comprises a through hole corresponding to the second open side of the structure and an adhesive area around the through hole.

* * * * *